United States Patent [19]

Kurbanov et al.

[11] 4,328,208

[45] May 4, 1982

[54] VACCINE AGAINST CHLAMYDOUS INFECTIONS OF FARM ANIMALS

[76] Inventors: Ildus A. Kurbanov, Nauchny gorodok, 1, kv. 6; Rasikh K. Jusupov, Nauchny gorodok, 1, kv. 35, both of Kazan; Roman V. Borovik, ulitsa Lunacharskogo, 37, kv. 9, Serpukhov, Moskovskaya oblast; Talgat G. Gabdulkhaev, Nauchny gorodok, 2, kv. 11; Ilmira A. Kurbanova, ulitsa Sibirsky trakt, 8, kv. 47, both of Kazan, all of U.S.S.R.

[21] Appl. No.: 265,559

[22] Filed: May 20, 1981

[51] Int. Cl.³ .................. A61K 39/118; A61K 31/78
[52] U.S. Cl. ..................................... 424/88; 424/89; 424/92; 424/81
[58] Field of Search ..................... 424/88–92

[56] References Cited

U.S. PATENT DOCUMENTS

| | | | |
|---|---|---|---|
| 3,767,790 | 10/1973 | Guttag | 424/92 |
| 3,869,546 | 3/1975 | Lund | 424/92 |
| 3,983,229 | 9/1976 | Relyveld | 424/92 |
| 4,021,364 | 5/1977 | Speiser et al. | 424/89 |
| 4,070,454 | 1/1978 | Relyveld | 424/89 |
| 4,071,619 | 1/1978 | Peradze et al. | 424/89 |
| 4,075,321 | 2/1978 | Relyveld | 424/92 |
| 4,225,581 | 9/1980 | Kreuter et al. | 424/89 |
| 4,252,792 | 2/1981 | Blades | 424/89 |
| 4,267,170 | 5/1981 | Seawell | 424/88 |
| 4,271,146 | 6/1981 | Seawell | 424/89 |

FOREIGN PATENT DOCUMENTS

| | | | |
|---|---|---|---|
| 14238 | 8/1980 | European Pat. Off. | 424/81 |
| 916803 | 1/1963 | United Kingdom | 424/89 |
| 940260 | 10/1963 | United Kingdom | 424/89 |
| 628924 | 9/1978 | U.S.S.R. | 424/81 |
| 661017 | 5/1979 | U.S.S.R. | |
| 666202 | 6/1979 | U.S.S.R. | |

OTHER PUBLICATIONS

Frank, F. W. et al. Am. J. Vet. Res. 29:1441–1446 Jul. 1968.
Senyk, G. et al. Med. Microbiol. Immunol. 168(2):91–102 (1980).
McEwen, A. D. et al. Vet. Rec. 68:686–691 (1956).
McEwen, A. D. et al. Vet. Rec. 63:197–201 (1951).
Valder, W. A. et al. Deutsche Tierarztliche Wochenschrift 82(6):221–225 (1975).
Sorodoc, G. et al. Revue Roumaine de Medecine, Virologie 30(2):131–134 (1979).
Schutte, A. P. et al. J. So. Afr. Vet. Assoc. 48(4):261–265 (1977).
Shewen, P. E. et al. Can. J. Comp. Med. 44(3):244–251 (1980).
Storz, J. (1971) Chlamydia and Chlamydia-induced diseases, 358 pp. C. C. Thomas, Springfield, Ill.
McKercher, D. G. et al. Cornell Vet. 59:211–226 (1969).
McKercher, D. G. et al. Cornell Vet. 56:433–450 (1966).
Rodolakis, A. et al. Annales de Recherches Veterinaires 10(1):41–48 (1979).
Yilmaz, S. et al. Berliner und Munchener Tierarztliche Wochenschrift 86(19):361–366 (1973).
McKercher, D. G. et al. J. Inf. Dis. 28(2):231–234 (1973).
Becerra, V. M. et al. Canad. J. Comp. Med. 40(1):46–52 (1976).
Kurbanov, I. A. et al. Veterinariya (Moscow) No. 2 (1978):66–70.
Borovik, R. V. et al. Vopr. Virusol. (4):485–488 (1978).
Borovik, R. V. et al. S–KH Biol. 10(1):107–109 (1975).

Primary Examiner—Shep K. Rose
Attorney, Agent, or Firm—Burgess, Ryan and Wayne

[57] ABSTRACT

The vaccine against chlamydous infections consists of an inactivated suspension of cells of yolk sacks of chicken embryos infected with a chlamydous infectant in a physiological solution or a phosphate buffer solution and an adjuvant; as the latter use is made of an aqueous solution of a mixture of tris-hydroxymethylaminomethane and tetramethylethylene diamine, an aqueous solution of a mixture of acrylamide and methylbisacrylamide, an aqueous solution of ammonium persulphate and an aqueous solution of glutaric aldehyde the components being present in the following proportions, ml

| | |
|---|---|
| antigenous liquid of an inactivated suspension of cells of yolk sacks of chicken embryos infected with a chlamydous infectant | 8–10 |
| aqueous solution of a mixture of tris-hydroxymethylaminomethane and tetraethylenediamine in a weight ratio of 15–16:1 respectively | 1–2 |
| aqueous solution of a mixture of acrylamide and methylbisacrylamide in a weight ratio of 37–38:1 respectively | 3–4 |
| 1.4% aqueous solution of ammonium persulphate | 1–2 |
| 25% aqueous solution of glutaric aldehyde | 0.026–0.028 |
| physiological solution or phosphate buffer solution - in an amount equal to the total amount of the above-mentioned components. | |

A method for prophylaxis of chlamydous infections of farm animals comprising administration of the above-specified vaccine to animals hypodermally or intramuscularly once in doses: for cattle—5 ml, for small cattle—1–2 ml.

3 Claims, No Drawings

VACCINE AGAINST CHLAMYDOUS INFECTIONS OF FARM ANIMALS

The present invention relates to veterinary biological preparations and, more specifically, it relates to a vaccine against chlamydous infections of farm animals and can be useful for the specific prophylaxis of chlamydous infections of farm animals and for the preparation, with these infections, of the immune serum.

Known in the art are vaccine against chlamydous abortions of sheep consisting of inactivated suspensions of yolk sacks of chicken embryos infected with chlamydiosis infectant with the addition of an oily adjuvant (cf. J. Storz Chlamydia and Chlamydia-Induced Diseases, 1971, p. 270–279).

A disadvantage of the prior art vaccines resides in a weak immunogeneity thereof, insufficiently restrained immunity, multiple vaccination of animals, separation of the oily adjuvant from the immunogenic mass thickening of the oily adjuvant at low temperatures ($+4°$ C.), causing the necessity of preheating the vaccine for the passage thereof through the injection needle, and restricted field of application of the vaccines to only one animal species.

It is an object of the present invention to provide a vaccine against chlamydous infections of all species of farm animals which would possess a prolonged effect and a high immunogenic activity.

This object is accomplished by that the vaccine against chlamydous infections of farm animals containing and antigenous liquid of an inactivated suspension of cells of yolk sacks of chicken embryos infected with a chlamydia infectant in a physiologcial solution or a phosphate-buffer solution and an adjuvant, according to the present invention, contains as the adjuvant an aqueous solution of a mixture of tris-hydroxymethylaminometane and tetramethylethylene diamine, an aqueous solution of a mixture of acrylamide and methylbisacrylamide, an aqueous solution of ammonium persulphate and an aqueous solution of glutaric aldehyde, the components being present in the following proportions, ml:

| | |
|---|---|
| antigenous liquid of an inactivated suspension of cells of yolk sacks of checken embryos infected with chlamydia infectant | 8 to 10 |
| aqueous solution of a mixture of tris-hydroxymethylaminomethane and tetramethylethylene diamine in a weight ratio of from 15:1 to 16:1 respectively | 1 to 2 |
| aqueous solution of a mixture of acrylamide and methylbisacrylamide in a weight ratio of 37:1 to 38:1 respectively | 3 to 4 |
| 1.4% aqueous solution of ammonium persulphate | 1 to 2 |
| 25% aqueous solution of glutaric aldehyde | 0.026 to 0.038 |
| physiological solution or phosphate buffer solution | in an amount equal to the total amount of the above-specified components. |

Inactivation of the suspension of cells of yolk sacks of chicken embryos infected with chlamydia infectant can be effected by means of conventional inactivators, namely merthiolate.

As the antigenous liquid the vaccine according to the present invention preferably contains a suspension of cells of yolk sacks of chicken embryos infected with chlamydia infectant and inactivated with merthiolate to the content thereof in the suspension of 0.05% by weight and formaldehyde to the content thereof in the suspension of 0.15% by weight. The incorporation, into the vaccine composition, of a new adjuvant makes it possible to effect polymerization of protein components of chlamydia shells while retaining their antigenous activity. The protein polymerization lowers its solubility simultaneously increasing antigeneous properties of protein structures of chlamydiae. One of the most important conditions of enahncing the immunogeneous properties of antigens is their corpusculation, i.e. creation of such a macromolecular structure of the antigen which would be suitable for interaction with macrophagous blood form elements. Insoluble aggregated antigens possess higher activity as compared to low-molecular soluble antigens. In the case of corpusculation of the antigen, its transformation to the aggregated state capable of withstanding enzymatic cleavage of tissues with enzymes is obtained by inclusion of chlamydiae into a synthetic gel of polyacrylamide. At the same time, preconditions are created for the formation of an antigenous depot in the organism. All this imparts a high immunogenic activity of a prolonged effect to the vaccine according to the present invention.

The vaccine of the present invention is produced in the following manner.

A suspension of yolk sacks of chicken embryos infected with chlamydia infectant is prepared. As the infectant use can be made of any kind of chlamydous infections.

The yolk scks of chicken embryos infected with chlamydia infectant are then subjected to the determination of the infectant titre by infection into yolk of 6–7 days' age chicken embryos. A high immunogeneity of the vaccine prepared from infected yolk sacks of chicken embryos with the chlamydia titre $ELD_{50}$ (embryo of lethan doses) of $10^{6.5}$ to $10^{7.0}$ has been proved experimentally.

Yolk sacks of chicken embryos are infected in a dose of 0.25 to 0.3 ml with the infectant titre of from $10^{6.5}$ to $10^{7.0}$ $ELD_{50}$ per each embryo. The suspension is prepared using a sterile 0.2 M phosphate buffer with a pH of 7.6–7.8, physiological solution or Hanks' buffer solution.

The resulting suspension is settled at the temperature of 4° C., the liquid over the residue is removed by suction and transferred into a sterile vessel, whereinto the inactivator is added. As the inactivator use can be made of a solution of merthiolate (1:5,000) to the final concentration of merthiolate in the suspension of 0.1% by weight or merthiolate in combination with formaldehyde to the final concentration of merthiolate of 0.05% and that of formaldehyde of 0.15% by weight in the suspension. The resulting mixture is kept, for inactivation of the infectant, in a thermostat at the temperature of 37° C. for 10–12 hours or in a refrigerator at a temperature of from 4° to 6° C. for 16 to 18 hours while periodically shaking the mixture.

Thereafter the adjuvant is added to the inactivated suspension. To this end, the following solutions are preliminary prepared: the first solution "A" comprises a mixture of tris-hydroxymethylaminomethane with tetramethylethylene diamine taken in a weight ratio of 15:1 to 16:1 respectively dissolved in sterile distilled water.

The second solution "C" comprises a mixture of acrylamide and methylbisacrylamide taken in a weight ratio of 37:1 to 38:1 respectively. The solutions "A" and "C" are stable for one month when stored at the temperature of 5° C.

These solutions are successively introduced into the inactivated suspension, then added with a 1.4% aqueous solution of ammonium persulphate and 25% solution of glutaric aldehyde.

The mixture is thoroughly intermized and kept in a refrigerator at a temperature of from 4° to 6° C. for 16 to 18 hours or in a thermostat at the temperature of 37° C. for 2-3 hours. During this period the vaccine mass is polymerized in the polyacrylamide gel. The resulting polymerized vaccine mass in the polyacrylamide gel is homogenized in homogenizers or colloidal mills with the equal volume of a sterile physiological solution (pH=7.2 to 7.4) or Hank's solution to a slurry-like consistence capable of passing through an injection needle. The thus-prepared vaccine is packed into flasks under sterile conditions.

The vaccine according to the present invention has been tested on various species of farm animals.

For prophylactic purposes, it is advisable that the vaccine according to the present invention be administered to farm animals once intramuscularly or hypodermally: to cattle in the dose of 5 ml, to small cattle—in a dose of 1-2 ml.

For a better understanding of the present invention, some specific examples illustrating tests of the vaccine and the method for preparing same according to the present invention are given hereinbelow.

EXAMPLE 1

There are prepared 100 ml of a 20% suspension of yolk sacks of chicken embryos infected with the infectant Chlamydiae, strain "250", in sterile Hanks' buffer solution. The resulting suspension is settled at the temperature of 4° C. for 2 hours. The liquid over the residue is sucked by a sterile pipette and transferred into a sterile flask. The resulting antigenous liquid is imspected for the absence of foreign microflora by inoculation onto Marten's broth, followed by residence in a thermostat at the temperature of 37° C. for 6 days. The broth shall be clear and give no rise to foreign microflora. Then into the antigenous liquid over the residue in the volume of 80 ml an aqueous solution of merthiolate is added to its final concentration of 0.05% by weight and formaldehyde to its concentration of 0.15% by weight in the antigenous liquid.

The mixture is maintained in a thermostat at the temperature of 37° C. for a period of from 10 to 14 hours. Then the adjuvant is introduced into the mixture.

To this end, the following solutions are prepared: Solution "A": to 48 ml of a 1 N solution of hydrochloric acid there are added 36.3 g of tris-hydroxymethylaminomethane, 0.23 ml of tetramethylethylene diamine and brought to 100 ml with sterile distilled water with pH of 8.9. Solution "C": 30 g of acrylamide and 0.8 g of methenebisacrylamide are distilled in sterile distilled water to 100 ml. Solutions "A" and "C" are stable for one month, provided that they are stored at the temperature of 5° C.

Then to 80 ml of the antigenous liquod there are successively added 10 ml of solution "A" and 30 ml of solution "C", 10 ml of 1.4% solution of ammonium persulphate and 25% solution of glutaric aldehyde to the final concentration thereof of 0.05% by weight in the antigenous liquid. The mixture after thorough stirring is placed into a thermostat at the temperature of 37° C. for 2-3 hours. The resulting polymerized vaccine mass in the polyacrylamide gel in the amount of 130 ml is homogenized with the equal volume of the Hanks' solution to a slurry-like consistence capable of passing through an injection needle. The resulting vaccine is tested for toxicity and immunogeneity. The testing of toxicity and immunogeneity of the vaccine according to the present invention is effected on white mice or pregnant guinea pigs by way of intraperitoneal administration of the vaccine to white mice (weighing 10-15 g) in the amount of 0.25 ml, to pregnant guinea pigs—in the amount of 0.5 ml, followed by intraperitoneal infection of these animals with an infectant out of the group of chlamydiae, strain "250". One third portion ($\frac{1}{3}$) of the animals are not vaccinized. The control non-vaccinized animals (white mice) have died, while pregnant guinea pigs have aborted. The vaccinized white mice survive, while vaccinized pregnant guinea pigs give healthy brood.

EXAMPLE 2

There are prepared 120 ml of a 40% suspension of yolk sacks of chicken embryo infected with the infectant Chlamydiae, strain 250, in a sterile physiological solution with pH of 7.6-7.8. The resulting suspension is settled at the temperature of 4° C. for 2 hours. The liquid over the residue is sucked by means of a sterile pipette and transferred into a sterile flask. The control for the absence of foreign microflora is effected following the procedure described in the foregoing Example 1. Then into the overresidue antigenous liquid in the volume of 100 ml an aqueous solution of merthiolate is added to the final concentration of 0.1% by weight. The mixture is kept in a refrigerator at a temperature of from 4° to 6° C. for 16 to 18 hours. Then the adjuvant is added to the mixture. Solutions "A" and "C" are preliminary prepared in a manner similar to that described in Example 1. Then to 100 ml of the antigenous liquid there are successively added 20 ml of solution "A", 40 ml of solution "C", 20 ml of 1.4% solution of ammonium persulphate and 25% solution of glutaric aldehyde to the final concentration thereof in the antigenous liquid of 0.05% by weight. The mixture after thorough stirring is kept in a refrigerator at a temperature of 4° to 6° C. for 16 to 18 hours. The resulting polymerized vaccine mass in the polyacrylamide gel in the amount of 180 ml is homogenized with the equal volume of physiological solution to a slurry-like consistence capable of passing through an injection needle. The resulting vaccine is tested for toxicity and immunogeneity in a manner similar to that described in Example 1 hereinbefore.

EXAMPLE 3

The vaccine of the present invention has been tested on bulls, sheep and pregnant heifers. A portion of the nonvaccinized cows has been used for control. According to the literature data and our own researches the infectant of abortion in cows from the group of chlamydiae is also pathogenic for sheep.

Both vaccines have been hypodermally injected to bulls, pregnant heifers in the dose of 5 ml and to sheep in the dose of 2 ml. The assessment of the vaccine efficiency has been made according to clinical and immunological characteristics and the results of the control infection. Blood for the preparation of serum has been taken twice before the vaccination and on the 5th, 11th day after the vaccination and then on the 3, 8, 12, 19th day after the infection. The vaccinized bulls, sheep and pregnant heifers have been infected with a live infectant of chlamydiae, strain 250.

No clinical symptoms have been noticed in the vaccinized animals. Serological studies in the reaction of complement binding, the complement-binding antibodies have been revealed in vaccinized sheep, bulls and pregnant heifers already on the 5th and 11th day in a titre of from 1:16 to 1:128. The control infection of the non-vaccinized animals (sheep, bulls, pregnant heifers) is accompanied by a total suppression of the animals, flabbiness, hypodynamics, reduced appetite and increased general body temperature to 41° C.–41.5° C. Within one week all the above-indicated pathological changes passed. The pregnant non-vaccinized heifers after the infection have aborted or brough before time weak, nonvital calves which died within three days after calving. In all of them the delay in afterbirth emission.

In the vaccinized bulls, sheep and pregnant heifers after the control infection no pathology in the general condition has been noticed. The pregnant heifers have calved in time and brought normal well-developed calves.

The vaccine ensures the antigenous activity and creates immunity in the vaccinized animals against the experimental infection.

In a similar manner 4 series of tests have been performed.

What is claimed is:

1. A vaccine against chlamydous infections of farm animals consisting of an inactivated suspension of cells of yolk sacks of chicken embryos infected with a chlamydous infectant in a physiological solution or a phosphate buffer solution and an adjuvant; the latter being an aqueous solution of a mixture of tris-hydroxymethylaminomethane and tetramethylethlene diamine, an aqueous solution of a mixture of acrylamide and methylbisacrylamide, an aqueous solution of ammonium persulphate and an aqueous solution of glutaric aldehyde, the components being present in the following proportions, ml:

| | |
|---|---|
| antigenous liquid of inactivated suspension of cells of yolk sacks of chicken embryos infected with chlamydous infectant | 8 to 10 |
| aqueous solution of a mixture of tris-hydroxymethylaminomethane and tetramethylethylene diamine in a weight ratio of 15:1 to 16:1 respectively | 1 to 2 |
| aqueous solution of a mixture of acrylamide and methylbisacrylamide in a weight ratio of 37:1 to 38:1 respectively | 3 to 4 |
| 1.4% aqueous solution of ammonium persulphate | 1 to 2 |
| 25% aqueous solution of glutaric aldehyde | 0.026 to 0.028 |
| physiological solution or phosphate buffer solution in an amount equal to | the total amount of the above components. |

2. A vaccine according to claim 1, wherein as the antigenous liquid a suspension of cells of yolk sacks of chicken embryos is used, sais suspension being infected with a chlamydous infectant and said embryos being inactivated with merthiolate to the content thereof in the suspension of 0.05% by weight and formaldehyde to a content thereof of 0.15% by weight.

3. A method of prophylaxis of chlamydous infections of farm animals comprising administration of the vaccine as claimed in claims 1 or 2 to animals hypodermally or intramuscularly one in doses: for cattle—5 ml, for small cattle—1–2 ml.

* * * * *